United States Patent [19]

Angenendt et al.

[11] Patent Number: 5,227,527
[45] Date of Patent: Jul. 13, 1993

[54] PROCESS FOR THE PREPARATION OF 3'-AMINOPROPYL 2-CHLOROETHYL SULFONE SEMISULFATE

[75] Inventors: Heinrich Angenendt; Michael Meier, both of Frankfurt am Main, Fed. Rep. of Germany

[73] Assignee: Hoechst Aktiengesellschaft, Frankfurt am Main, Fed. Rep. of Germany

[21] Appl. No.: 896,322

[22] Filed: Jun. 10, 1992

[30] Foreign Application Priority Data

Jun. 12, 1991 [DE]  Fed. Rep. of Germany ....... 4119287

[51] Int. Cl.$^5$ ............................................. C07C 315/02
[52] U.S. Cl. .................................... 564/496; 564/500
[58] Field of Search .................. 568/30; 564/496, 500

[56] References Cited

U.S. PATENT DOCUMENTS

| 2,824,887 | 2/1958 | Klopping | 568/30 |
| 4,709,018 | 11/1987 | Seitz | 568/30 |
| 4,841,028 | 6/1989 | Aeschlimann et al. | 568/30 |

FOREIGN PATENT DOCUMENTS

WO91-13866  9/1991  PCT Int'l Appl. .

*Primary Examiner*—Robert W. Ramsuer

[57] ABSTRACT

A process for the preparation of 3'-aminopropyl 2-chloro-ethyl sulfone semisulfate in very good yield and high purity, by reacting allylamine with mercaptoethanol in a one-pot process in about 0.5 to about 0.6 mol of dilute sulfuric acid, relative to allylamine, at temperatures of about 0° C. up to the boiling point of the reaction mixture in the presence of a free-radical initiator, introducing 2.0 to about 2.5 mol of chlorine into the resultant reaction mixture at temperatures of about 0° C. to about 100° C. and then concentrating the mixture obtained to dryness.

13 Claims, No Drawings

PROCESS FOR THE PREPARATION OF 3'-AMINOPROPYL 2-CHLOROETHYL SULFONE SEMISULFATE

DESCRIPTION

The invention relates to a process for the preparation of 3'-aminopropyl 2-chloroethyl sulfone in the form of the semisulfate in very good yield and high purity, by reacting allylamine with mercaptoethanol in a one-pot process in dilute sulfuric acid in the presence of a free-radical initiator, introducing chlorine into the mixture produced and then concentrating the mixture obtained to dryness.

3'-Aminopropyl 2-chloroethyl sulfone is an important precursor for the preparation of reactive dyes (EP 141 776, EP 174 909 and EP 208 655). The preparation of 3'-aminopropyl 2-chloroethyl sulfone has not yet been described in the literature. However, the preparation of 2'-aminoethyl 2-chloroethyl sulfone hydrochloride is disclosed in the literature. In this case, according to U.S. Pat. No. 824 887, 2-chloroethylamine hydrochloride is reacted with the sodium salt of mercaptoethanol and the 2'-aminoethyl 2-hydroxyethyl sulfide thus obtained is chlorinated with thionyl chloride to give 2'-aminoethyl 2-chloroethyl sulfide hydrochloride, which is then oxidized with peracetic acid to give 2'-aminoethyl 2-chloroethyl sulfone hydrochloride. 2'-Aminoethyl 2-hydroxyethyl sulfide can also be reacted by processes disclosed in the literature (for example Izv. Akad. Nauk. SSSr, Ser. Khim, 1976, 4, 937-940 and EP Patent 015 929 (page 80/81, example 88)) by chlorination and oxidation with chlorine to give 2'-aminoethyl 2-chloroethyl sulfone hydrochloride.

If it were desired to prepare 3'-aminopropyl 2-chloroethyl sulfone in an analogous fashion, it would have to be accepted that the preparation of 3'-aminopropyl 2-hydroxyethyl sulfide would be accompanied by the production of two equivalents of sodium chloride, which would have to be laboriously separated with high losses at the sulfide step or the final step.

In the course of a chlorination with thionyl chloride and subsequent oxidation with peracetic acid analogously to U.S. Pat. No. 2,824,887, a further one equivalent each of sulfur dioxide and hydrogen chloride would, in addition, be inevitably produced.

It should thus be noted that these processes do not comply with the current requirements for an industrial process. A need therefore existed for an economical process which is easily carried out industrially for the preparation of 3'-aminopropyl 2-chloroethyl sulfone.

It has now surprisingly been found that 3'-aminopropyl 2-choroethyl sulfone can be advantagiously prepared in the form of the semisulfate in very good yield (>95% of theory) and in high purity be reacting allylamine with mercaptoethanol in a one-pot process in 0.5 to about 0.6 mol, preferably 0.50 to about 0.55 mol, of dilute (aqueous) sulfuric acid, relative to allylamine, at temperatures of about 0° C. up to the boiling point of the reaction mixture, preferably from about 45° C. to about 80° C., in the presence of a free-radical initiator, introducing 2.0 to about 2.5 mol, preferably 2.0 to about 2.1 mol, of chlorine into the resultant reaction mixture at temperatures of about 0° C. to about 100° C., preferably from about 40° C. to about 80° C., and then concentrating the mixture obtained to dryness.

The process according to the invention is described by the reaction scheme below:

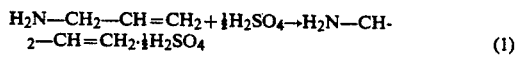

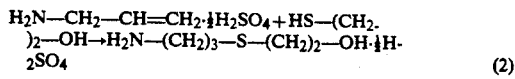

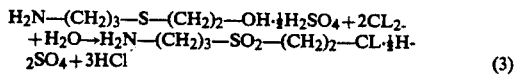

The concentration of the dilute (aqueous) sulfuric acid in which the reaction is carried out is expediently in the range between about 10% and about 50%, preferably about 20% and about 40%. At concentrations >50%, precipitations can occur during the reaction; concentrations <10% are not economically justifiable because of poorer space-time yields.

As far as the quantitative proportions are concerned, it is expedient to initally introduce 1.0 mol of allylamine in about 0.5 to about 0.6 mol, preferably about 0.50 to about 0.55 mol, of dilute (aqueous) sulfuric acid at a temperature within the abovementioned ranges, at which the free-radical initiator used has a half life of about 1–5 hours, and to meter in about 0.9 to about 1.5 mol, preferably about 0.95 to about 1.05 mol, of mercaptoethanol, about 0.1 to about 5.0 g, preferably about 0.5 to about 1.5 g, of free-radical initiator being dissolved per mol of mercaptoethanol. It is also possible to take mercaptoethanol, about 0.1 to about 5.0 g, preferably about 0.5 to about 1.5 g, of free-radical initiator being dissolved per mol of mercaptoethanol, and to meter in 1.0 mol of allylamine in about 0.5 to about 0.6 mol, preferably about 0.5 to about 0.55 mol, of dilute (aqueous) sulfuric acid at a temperature at which the free-radical initiator has a half life of about 1 to 5 hours. However, a procedure can also be followed in which 1.0 mol of allylamine is taken in about 0.5 to about 0.6 mol, preferably about 0.50 to about 0.55 mol, of dilute (aqueous) sulfuric acid and about 0.1 to about 1.0 mol of mercaptoethanol at a temperature within the abovementioned ranges at which the free-radical initiator has a half life of 1 to 5 hours, and to meter in about 0.1 to about 5.0 g, preferably about 0.5 to about 1.5 g, of free-radical initiator per mol of mercaptoethanol dissolved in the remaining mercaptoethanol or in water. Alternatively, all components can be introduced together, but this is critical for an industrial procedure because of the heat of reaction liberated.

The free-radical initiators are preferably those which are soluble in the reaction medium, such as for example 2,2'-azobis[2-(2-imidazolin-2-yl)propane] dihydrochloride or 2,2'-azobis-(2-amidinopropane) dihydrochloride. It is also possible to use free-radical initiators which form sulfates with sulfuric acid that are soluble in the reaction medium, such as for example 2,2'-azobis[2-(2-imidazolin-2-yl) propane].

The process according to the invention is expediently carried out at atmospheric pressure; however, a procedure employing elevated or reduced pressure is likewise possible.

It is an advantage of the process according to the invention that no waste products are formed, apart from the hydrochloric acid which is distilled off and can be reused, and that the reaction is carried out as a one-pot process, the 3'-aminopropyl 2-chloroethyl sulfone semisulfate being produced without further purification in surprisingly high yield (>95% of theory) and purity (>98%), which makes the process very favorable from the economic and ecological point of view.

The invention is illustrated in more detail by means of the examples below, without being restricted thereto.

EXAMPLE 1

400 g of ice and 204 g (2.0 mol) of 96% strength sulfuric acid are introduced into a 2 l four-neck flask equipped with stirrer, dropping funnel, thermometer and reflux condenser. 228 g (4.0 mol) of allylamine are then run in. 312 g (4.0 mol) of mercaptoethanol are then added and the batch is heated to 55° C. A solution of 4.0 g of 2,2'-azobis[2-(2-imidazolin-2-yl)propane] dihydrochloride in 50 ml of water is metered in to the mixture at 55° C. in the course of 15 min. After the reaction is completed, 300 ml of water are added and 580 g (8.2 mol) of chlorine are passed into the solution at 50° C. in 4 hours. The mixture is then evaporated in vacuo and 1038 g of wet, colorless 3'-aminopropyl 2-chloroethyl sulfone semisulfate are obtained having a content of 87.3% and a purity >98% (according to elemental analysis), corresponding to a yield of 96.5% of theory.

IR(KBr): 875, 1050, 1125, 1210, 1290, 1515, 1630, 2920, 2980, 3070, 3200 cm$^{-1}$.

$^1$H—NMR(D$_6$DMSO):$\delta$=2.03 (tt,J=7.0 Hz;2H,CH$_2$—C$\underline{H}_2$—CH$_2$),2.93CM;2H,C$\underline{H}_2$—NH$_3$+),- 3.35(t,J=7.0Hz;2H,SO$_2$—C-H$_2$—CH$_2$—Cl),3.96(t,J=7.0Hz;2H,C$\underline{H}_2$—CL),8.0(M,-broad;3H,NH$_3$+).

| Elemental analysis (wet product, 87% strength): | | |
|---|---|---|
| | Calculated: | Found: |
| C | 22.3% | 22.4% |
| N | 5.2% | 5.2% |
| S | 17.9% | 17.9% |
| Cl(organic) | 13.2% | 13.0% |

EXAMPLE 2

400 g of ice and 204 g (2.0 mol) of 96% strength sulfuric acid are introduced into a 2 l four-neck flask equipped with stirrer, dropping funnel, thermometer and reflux condenser. 228 g (4.0 mol) of allylamine are then run in. 312 g (4.0 mol) of mercaptoethanol are then added and the batch is heated to 70° C. A solution of 4.0 g of 2,2'-azobis(2-amidinopropane) dihydrochloride in 50 ml of water is metered in to the mixture at 70° C. in the course of 15 min. After the reaction is completed, 300 ml of water are added and 580 g (8.2 mol) of chlorine are passed into the solution at 50° C. in 4 hours. The mixture is then evaporated in vacuo and 1009 g of wet 3'-aminopropyl 2-chloroethyl sulfone semisulfate are obtained having a content of 89.8% and a purity >98% (according to elemental analysis), corresponding to a yield of 96.1% of theory.

The spectroscopic data are identical to those given in Example 1.

We claim:

1. A process for the preparation of 3'-aminopropyl 2-chloroethyl sulfone semisulfate in very good yield and high purity, which comprises reacting allylamine with mercaptoethanol in a one-pot process in about 0.5 to about 0.6 mol of dilute (aqueous) sulfuric acid, relative to allylamine, at temperatures of about 0° C. up to the boiling point of the reaction mixture in the presence of a free-radical initiator, introducing 2.0 to about 2.5 mol of chlorine into the resultant reaction mixture at temperatures of about 0° C. to about 100° C. and then concentrating the mixture obtained to dryness.

2. The process as claimed in claim 1, wherein the first reaction step is carried out at temperatures of about 45° C. to about 80° C.

3. The process as claimed in claim 1, wherein chlorine is passed in at temperatures of about 40° C. to about 80° C.

4. The process as claimed in claim 1, wherein the reaction of allylamine with mercaptoethanol in dilute (aqueous) sulfuric acid is carried out at the temperature at which the free-radical initiator has a half life of about 1 to about 5 hours.

5. The process as claimed in claim 1, wherein the free-radical initiator used is 2,2'-azobis[2-(2-imidazolin-2-yl)propane] dihydrochloride.

6. The process as claimed in claim 1, wherein the free-radical initiator used is 2,2'-azobis(2-amidinopropane) dihydrochloride.

7. The process as claimed in claim 1, wherein the free-radical initiator used is 2,2'-azobis[2-(2-imidazolin-2-yl)propane].

8. The process as claimed in claim 1, wherein the treatment with chlorine is carried out at temperatures from about 40° to about 80° C.

9. The process as claimed in claim 1, wherein the first reaction step is carried out in about 10 to about 50% strength aqueous sulfuric acid.

10. The process as claimed in claim 1, wherein the first reaction step is carried out in about 20 to about 40% strength aqueous sulfuric acid.

11. The process as claimed in claim 1, wherein 1.0 mol of allylamine is brought to reaction with about 0.9 to about 1.5 mol of mercaptoethanol in the presence of about 0.1 to about 5.0 g of free-radical initiator per mol of mercaptoethanol.

12. The process as claimed in claim 1, wherein the reaction is carried out at atmospheric pressure, in vacuo or at superatmospheric pressure.

13. The process as claimed in claim 1, wherein said free radical initiator has a half life of about 1 to 5 hours at 45° to 80° C. and is soluble in the reaction medium or, in the presence of the sulfuric acid, forms a sulfate which is soluble in the reaction medium.

* * * * *